US00PP10192P

United States Patent [19]

McAllister

[11] Patent Number: Plant 10,192

[45] Date of Patent: Jan. 13, 1998

[54] BRACHYCOME PLANT NAMED 'BILLABONG BRIGHT EYES'

[75] Inventor: Margaret McAllister, Croydon, Australia

[73] Assignee: Koala Blooms Pty. Ltd., Mordialloc, Australia

[21] Appl. No.: 690,593

[22] Filed: Jul. 31, 1996

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—C. A. Whealy

[57] ABSTRACT

A new and distinct cultivar of *Brachycome multifida* named 'Billabong Bright Eyes', characterized by its low-growing and spreading plant habit; fast crop time; freely branching plant habit; numerous inflorescences with purple ray florets and bright yellow disc florets; and long, erect peduncles that hold inflorescences above the foliage.

2 Drawing Sheets

1

The present invention relates to a new and distinct cultivar of Brachycome plant, botanically known as *Brachycome multifida* and referred to by the cultivar name Billabong Bright Eyes.

The new cultivar originated from a cross made by the inventor of the *Brachycome multifida* cultivar Dilatata (not patented), as the male or pollen parent, with the *Brachycome multifida* cultivar Breakoday (not patented), as the female or seed parent. The cultivar Billabong Bright Eyes was discovered and selected by the inventor as a flowering plant within the progeny of the stated cross in a controlled environment in Montrose, Victoria, Australia in 1990.

Asexual reproduction of the new cultivar by terminal cuttings taken in a controlled environment in Montrose, Victoria, Australia, has shown that the unique features of this new Brachycome are stable and are reproduced true to type in successive propagations.

The new cultivar has not been observed under all possible environmental conditions. The phenotype may vary somewhat with variations in environment such as temperature, daylength and light intensity, without, however, any variance in genotype.

Compared to the parent cultivar Dilatata, plants of the new Brachycome are taller, more vigorous, have larger flowers and have darker purple ray florets. Compared to the parent cultivar Breakoday, plants of the new Brachycome are more compact and have smaller inflorescences. A detailed comparison of the differences between the cultivars Billabong Bright Eyes and the cultivar Dilatata appears in Chart A at the end of the specification.

The following characteristics have been repeatedly observed and are determined to be basic characteristics of 'Billabong Bright Eyes' and which distinguish 'Billabong Bright Eyes' as a new and distinct cultivar:

1. Low-growing and spreading plant habit.
2. Fast crop time.
3. Freely branching plant habit.
4. Numerous inflorescences with purple ray florets and bright yellow disc florets.
5. Long, erect peduncles that hold inflorescences above the foliage.

The accompanying colored photographs illustrate the overall appearance of the new cultivar, showing the colors as true as it is reasonably possible to obtain in colored reproductions of this type.

The first photograph comprises a top perspective view of a single potted plant of 'Billabong Bright Eyes'.

The second photograph comprises a close-up view of inflorescences of plants of 'Billabong Bright Eyes'. Floret color in the photographs may appear different from the actual floret color due to light reflectance.

The following observations, measurements, values, and

2 comparisons describe plants grown in Montrose, Victoria, Australia, under outdoor conditions with day temperatures ranging from 15 to 30C, night temperatures ranging from 10 to 20C, and light levels ranging from 5,000 to 9,000 foot-candles. Color references are made to The Royal Horticultural Society Colour Chart except where general terms of ordinary dictionary significance are used.

Classification:

*Botanical.*—*Brachycome multifida* cultivar Billabong Bright Eyes.

*Commercial.*—Brachycome.

Parentage:

*Male or pollen parent.*—*Brachycome multifida* cultivar Dilatata.

*Female or seed parent.*—*Brachycome multifida* cultivar Breakoday.

Propagation:

*Type.*—By cuttings.

*Time to initiate and develop roots.*—Summer: 10 to 20 days at temperatures of 25C. Winter: 15 to 30 days at temperatures of 20C.

*Rooting habit.*—Fibrous and freely branching.

Plant description:

*General appearance.*—Low-growing, spreading, herbaceous plant with deeply pinnatifid foliage and erect flower stems. Appropriate for 12.5 pots to 25-cm hanging basket containers. To produce a 15-cm finished flowering plant from rooted cuttings, 8 to 12 weeks are required depending on temperature and light level.

*Plant height.*—10 to 15 cm from soil level to top of inflorescences.

*Branching.*—Freely branching, typically up to 5 lateral branches develop when the terminal apex is removed (pinched). Lateral branches are typically 4 to 10 cm in length.

*Growth rate.*—Moderate to rapid.

*Vigor.*—Moderate.

*Foliage description.*—Arrangement: Alternate, single. Quantity: 12 to 22 per lateral branch. Leaf shape: Deeply pinnatifid. Leaf apex: Acute to obtuse. Leaf base: Obtuse. Leaf margin: Pinnatifid. Leaf aspect: Flat. Leaf length: 1.4 to 2 cm. Leaf width: 1.3 to 1.7 cm. Leaf texture: Smooth, glabrous. Leaf attachment: Sessile. Leaf color: Young leaves: Abaxial surface: 138A. Adaxial surface: 138A. Fully expanded leaves: Abaxial surface: 141A. Adaxial surface: 14B. Venation: Abaxial surface: 138A. Adaxial surface: 14B.

Flowering description:

*Inflorescence.*—Single daisy-type composite inflorescence form. Florets arranged acropetally on a capitulum. Inflorescences last on the plant for 3 to 4 weeks and about 1 week as a fresh cut flower. Inflorescences semi-persistent.

*Natural flowering season.*—Natural flowering season is spring to fall. Plants flower continuously during this period.

*Quantity of inflorescences.*—One to five per lateral branch.

*Inflorescence diameter.*—1.7 to 2.1 cm.

*Inflorescence depth (height).*—About 8 mm.

*Fragrance.*—Slight.

*Ray florets.*—Quantity: 18 to 24 florets per inflorescence. Shape: Narrowly obovate. Apex: Obtuse. Margin: Entire. Length: 5 to 7 mm. Width: About 1 mm. Texture: Smooth, glabrous. Color: When opening, abaxial surface: 87A. Mature, abaxial surface: 87A. With further development, florets fade to 88C. Mature, adaxial surface: 87D.

*Disc florets.*—Shape: Tubular. Diameter of disc: 3 to 5 mm. Disc floret length: About 3 mm. Disc floret width: About 1 min. Color: Immature: 12C. Mature: 12B. Number of disc florets per inflorescence: Numerous.

*Peduncle.*—Length: 3 to 5.5 cm. Strength: Moderately strong, inflorescences held erect above foliage. Texture: Smooth, glabrous. Color: 144A.

*Flower bud.*—Shape: Globular. Length: About 4 mm. Diameter: About 3 mm. Color: 145C.

*Involucral bracts.*—Arrangement: Imbricated. Quantity: 10 to 12 per inflorescence. Shape: Elliptic to oblong. Apex: Obtuse. Margin: Ciliate. Texture: Smooth, glabrous. Color: Abaxial surface: 143C. Adaxial surface: 144B.

*Androecium.*—Stamen number: Five per floret. Anther shape: Linear. Pollen color: 14A.

*Gynoecium.*—Pistil number: One per floret. Stigma shape: Bilobate. Style length: 2 to 3 mm.

Disease resistance: No susceptibility nor resistance to fungal, bacterial or viral pathogens has been noted.

Seed production: Seed production is typically not observed.

CHART A

| CHARACTERISTIC | 'BILLABONG BRIGHT EYES' | 'DILATATA' |
|---|---|---|
| PLANT HEIGHT | 10 to 15 cm | 6 to 10 cm |
| LATERAL BRANCH LENGTH | 4 to 10 cm | 3 to 6.5 cm |
| QUANTITY OF LEAVES | 12 to 22 per lateral branch | 8 to 18 per lateral branch |
| LEAF COLOR, YOUNG LEAVES, ABAXIAL SURFACE | 138A | 143A |
| LEAF COLOR, YOUNG LEAVES, ADAXIAL SURFACE | 138A | 143A |
| LEAF COLOR, MATURE LEAVES, ABAXIAL SURFACE | 141A | 137A |
| LEAF COLOR, MATURE LEAVES, ADAXIAL SURFACE | 141B | 137C |
| LEAF LENGTH | 1.4 to 2 cm | 1.2 to 2 cm |
| LEAF WIDTH | 1.3 to 1.7 cm | 0.6 to 1.5 cm |
| QUANTITY OF INFLORESCENCES PER STEM | 1 to 5 | 1 to 3 |
| INFLORESCENCE DIAMETER | 1.7 to 2.1 cm | 0.9 to 1.4 cm |
| INFLORESCENCE DEPTH | About 8 mm | About 4.5 mm |
| RAY FLORET LENGTH | 5 to 7 mm | 3 to 5 mm |
| RAY FLORET WIDTH | About 1 mm | About 1 mm |
| RAY FLORET COLOR, OPENING | 87A | 86D |
| RAY FLORET COLOR, MATURE ABAXIAL SURFACE | 87A | 85A |
| RAY FLORET COLOR, MATURE ADAXIAL SURFACE | 87D | 85B |
| NUMBER OF RAY FLORETS PER INFLORESCENCE | 18 to 24 | 12 to 20 |
| DISC FLORET COLOR, IMMATURE | 12C | 20B |
| DISC FLORET COLOR, MATURE | 12B | 20B |
| PEDUNCLE LENGTH | 3 to 5.5 cm | 2 to 3.3 cm |

It is claimed:

1. A new and distinct cultivar of *Brachycome multifida* plant named 'Billabong Bright Eyes', as illustrated and described.

* * * * *

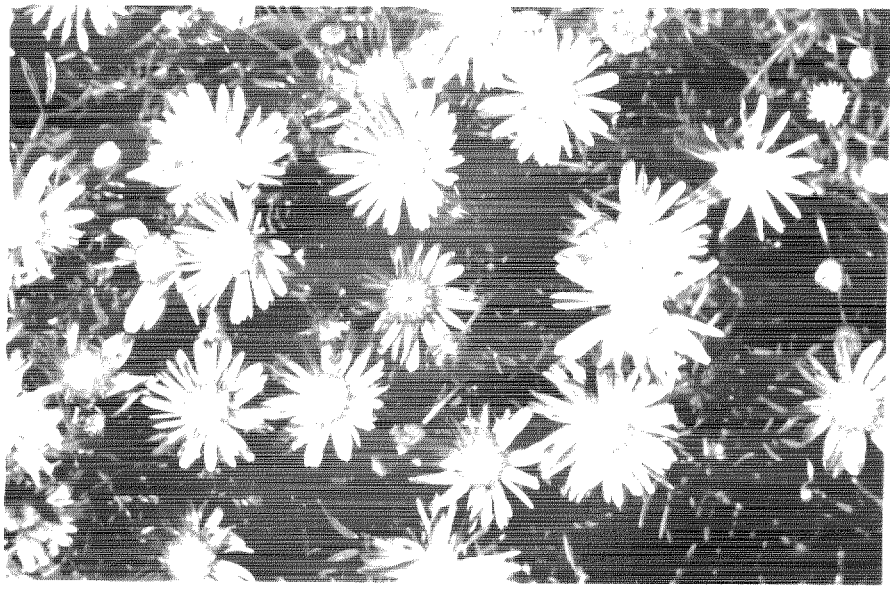

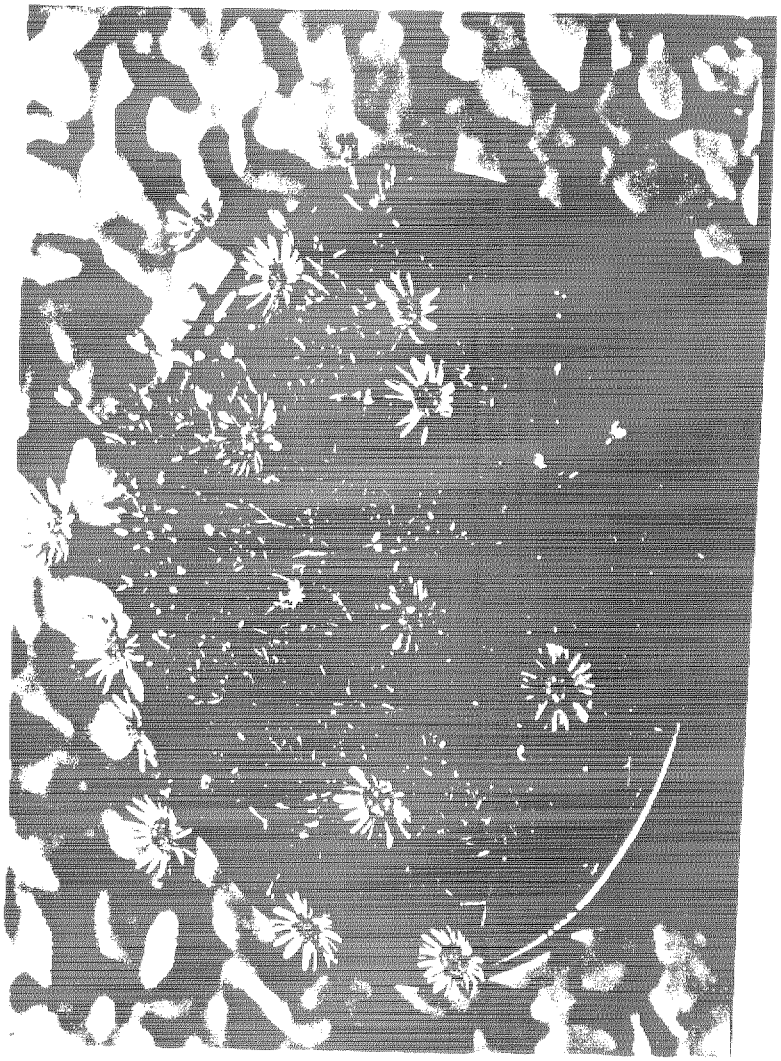

PLT-263
C5203 OR PP 010,192 SR